United States Patent [19]

Lee

[11] 4,158,677

[45] Jun. 19, 1979

[54] DIALKYLATION OF ALKYLBENZENE

[75] Inventor: Richard J. Lee, Downers Grove, Ill.

[73] Assignee: Standard Oil Company (Indiana), Chicago, Ill.

[21] Appl. No.: 924,144

[22] Filed: Jul. 13, 1978

[51] Int. Cl.$^2$ .............................................. C07C 3/56
[52] U.S. Cl. ...................................... 585/456; 585/465
[58] Field of Search ............ 260/671 R, 671 B, 671 C

[56] References Cited

U.S. PATENT DOCUMENTS

| | | | |
|---|---|---|---|
| 2,667,519 | 1/1954 | Paltz et al. ...................... | 260/671 B |
| 3,216,926 | 11/1965 | Kurtz et al. ........................... | 208/282 |

OTHER PUBLICATIONS

Chem. Abs. 67, 43084 (1967).
Chem. Abs. 82, 87406 (1975).

*Primary Examiner*—C. Davis
*Attorney, Agent, or Firm*—William H. Magidson; Arthur G. Gilkes; William T. McClain

[57] ABSTRACT

Dialkylation process for the manufacture of synthetic oils comprising contacting olefin with alkylbenzene in the presence of a borontrifluoride carboxylic acid complex.

10 Claims, No Drawings

DIALKYLATION OF ALKYLBENZENE

This invention relates to a dialkylation process for the manufacture of synthetic oils. More particularly this invention relates to a process of dialkylating alkylbenzene which comprises contacting olefin with alkylbenzene in the presence of a borontrifluoride carboxylic acid complex.

Trialkylated benzene containing from about twenty-five to forty carbon atoms in the total of the three alkyl groups is useful as a synthetic lubricant because it is characterized by high flash points and low viscosities at low temperatures. Trialkylated benzene is also used as an intermediate for the synthesis of sulfonate detergents or dispersants.

Alkylation of aromatics using a broad range of Friedel Crafts catalysts is well known. Known catalysts include Bronsted acids such as sulfuric, phosphoric, and hydrofluoric acids; Lewis acids such as the metal halides; and solid metal oxide catalysts such as silica-alumina, zinc chloride on alumina, or tungstic acid on silica containing acid sites of both Lewis and Bronsted types. The alkylation of aromatics with olefins is initiated by the interaction of a catalyst with an olefin to produce a carbonium ion which then reacts with the aromatic ring. Carbonium ions can undergo a number of typical reactions including addition to olefins to form polymers, carbon skeleton rearrangement, and hydride transfer. These reactions accompany the alkylation reaction in varying degrees and affect product distributions for specific alkylations. Also, product distribution is generally altered by concurrent isomerization and disproportionation. The initial orientation of the alkyl groups is influenced by the type and steric requirements of both the substituents already present and the entering group and by the reactivity of the alkylating agent. The severity of the reaction conditions, polar effects, and steric factors affect the extent of isomerization and disproportionation which occurs.

Because of this inter or intra molecular rearrangement of the alkyl groups, utilization of Friedel Crafts catalyzed alkylations requires a separation process to isolate the desired trialkylates from mono- and dialkylates also generated. Selectivity is necessary to obtain those properties advantageous in synthetic lubricants. Separation procedures for alkylate mixtures are normally complex and expensive, therefore creating a need for an alkylation process which proceeds without rearrangement of alkyl groups to minimize isolation problems.

The physical properties of borontrifluoride carboxylic acid complexes have been studied and their use as catalysts are known in the condensation of phenols and ketones and in the condensation of aromatic hydrocarbons in the production of petroleum resins. See British Pat. No. 941,995; U.S. Pat. No. 3,216,926; and Laurent, "Reaction Products of Boron Halides with Various Organic Molecules," *Ann. Chim.*, (Paris), 6, 677–731 (1961). None of these references suggest use of the complex as a dialkylation catalyst.

It is the general object of this invention to provide an improved method for the manufacture of synthetic oils. Another object of this invention is to provide a new process for generating high yields of benzene trialkylates. A further object is to provide a method for dialkylating alkylbenzene with olefin in the presence of a catalyst complex. Other objects appear hereinafter.

The objects of this invention can be obtained by reacting alkylbenzene with olefin in the presence of a borontrifluoride carboxylic acid catalyst. The reaction proceeds at room temperature with a preference for dialkylation. The resulting trialkylated benzene is easily separated from the reaction mixture and purified without complex isolation procedures.

The catalytic complex is composed of borontrifluoride and carboxylic acid. Suitable carboxylic acids include aliphatic carboxylic acids containing one to eight carbon atoms such as formic, acetic, propionic, caprylic and other homologs. Those existing as liquids at room temperature are preferred for ease of handling. Fluorine substituted aliphatic carboxylic acids such as trifluoroacetic acid are also suitable. Larger substituents on the acid such as chlorine, bromine, etc. are less desirable because the resulting steric hindrances in the borontrifluoride carboxylic acid complex decrease the stability of the complex. Formic acid is preferred as the acid component of the complex. The additional electron releasing alkyl groups of the higher homologs weaken these carboxylic acids and yield complexes correspondingly less effective. Formic acid is preferably used as a 97–98% aqueous acid, although concentrations as low as 90% acid are suitable. This minimizes the formation of borontrifluoride water complexes which have no catalytic effect in the alkylation reaction.

The borontrifluoride carboxylic acid complex can be prepared by known methods. Commonly a stream of borontrifluoride gas is bubbled through the carboxylic acid at ambient temperature and pressure. The borontrifluoride is absorbed in an exothermic reaction and after cooling to room temperature the complex is ready for use. The molar ratio of borontrifluoride to acid can vary from 1:1 to 1:3 with 1:2 being preferred. Ratios less than 1:2 require the use of pressures greater than atmospheric to keep the borontrifluoride in solution. The amount of pressure needed is inversely proportional to the number of carbon atoms in the acid. Use of a like amount of pressure in the alkylation reaction in which the catalyst is employed would be required. Ratios greater than 1:2 result in uncomplexed acid in the solution thereby increasing the potential for side reactions.

Aromatics appropriate as reactants include monosubstituted alkylbenzenes, such as toluene, ethylbenzene, propylbenzene and the like. Straight chained alkyl substituents such as methyl, ethyl, n-propyl, n-butyl, etc. are preferred to branched ones such as isopropyl, isobutyl, tertbutyl, and the like, to minimize steric hindrance in the alkylation reaction. Examples of the preferred alkylbenzenes include toluene, ethylbenzene, n-propylbenzene, n-butylbenzene, etc.

Olefins suitable as reactants include α-olefins of eight to forty carbon atoms such as the various isomers of octene-1 or polybutene. The α-olefins can be straight chained or branched containing primary, secondary, or tertiary alkyl groups such as methyl, ethyl, propyl, isopropyl, butyl, isobutyl, and the isomers of pentyl, hexyl, heptyl and the like. Monosubstituted, disubstituted cis, disubstituted trans, or trisubstituted polymers of olefins such as polypropylene or polybutene can be used. The viscosity of the olefin acts as a physical limitation in that any dilution necessary to achieve adequate contact for reaction also dilutes the catalyst reducing its effectiveness. Preferred are α-olefins of $C_{12}$–$C_{20}$ such as dodecene-1, polypropylene tetramer, eicosene-1, or polybutene pentamer. Olefins can be selected on the basis of cost and availability with the overall objective of generating a trialkylated benzene with from about twenty-five to a maximum of about forty carbons in the total of the three alkyl substituents. Distribution of the carbons within the three substituents can be random except that usually only one alkyl group can contain less than three carbons in order to attain the desired lubricant properties.

In somewhat greater detail trialkylates of benzene are produced by contacting monoalkylbenzene and α-olefin in the presence of a borontrifluoride carboxylic acid catalyst. The amount of olefin can range from one to six moles and use of an excess of olefins is desirable. The preferred molar ratio of "alkylbenzene:olefin" is 1:2 or greater due to the second order kinetics of the reaction. No significant loss in dialkylation occurs if the alkylbenzene:olefin ratio is decreased to as low as 1:1. If a ratio of greater than 1:6 is used solubility problems are incurred. The exothermic reaction proceeds at ambient temperature and pressure and is controlled by cooling if necessary. The trialkylates generated are separated from the catalyst by phase separation and purified by fractional distillation. Substantially no inter or intra molecular rearrangement of alkyl groups occurs to produce mono- or dialkylated benzene. Yields of 80-100% trialkylates of benzene are commonly obtained using this process.

Contacting the reactants consists of mixing the alkylbenzene and olefin in a reactor, usually glass or borontrifluoride resistant metals or coated metals. The borontrifluoride is complexed with the acid in a separate reaction as previously discussed and the catalyst can be added to the reactor before or after either or both of the reactants. Vigorous stirring is required to generate contact sufficient to effect the reaction. Heat can be used with the stirring to aid in the contacting of more viscous reactants but is not chemically necessary to initiate the reaction. The reactor can comprise part of an open or closed system for conductance of the dialkylation process.

Temperatures of from about 10° C. to 80° C. are suitable for carrying out the dialkylation reaction of alkylbenzene with olefin. The preferred range should be below the boiling point of the particular olefin employed as a reactant. The reaction is exothermic and the reaction mixture should be cooled to avoid damaging temperature rise. At all times the reaction mixture should be maintained below a maximum of 90°-95° C. to prevent decomposition of the catalyst. Stirring is continued throughout the reaction and for one to five days after the reaction mixture cools to room temperature. In order to assure completion of the reaction a minimum stirring time of one day is preferred.

The dialkylation reaction proceeds readily at atmospheric pressure. Development of slightly greater pressure, such as 2-3 atmospheres, when using a closed system is permissible. Pressure greater than atmospheric is necessary if the borontrifluoride carboxylic acid catalyst has a molar ratio of less than 1:2 in order to avoid catalyst decomposition, but this higher pressure does not affect the rate of reaction independently of the catalyst.

Separation is obtained by phase separation and fractional distillation. The polarity of the catalyst causes it to separate in phase from the trialkylated benzene on standing. Poor separations can be improved by adding an appropriate solvent such as a saturated hydrocarbon. The catalyst can then be siphoned for later reuse. The alkylate phase can be purified by washing with water or bubbling nitrogen gas through it to eliminate any dissolved catalyst. Any minor by-products formed or any residual alkylbenzene or olefin present are separated from the trialkylated benzene by fractional distillation.

Identification of the distillation fractions confirms that the dialkylation process occurs with substantially no inter or intra molecular rearrangement of alkyl groups. A high yield of trialkylates with substitution primarily ortho and para to the benzene alkyl substituent already present is obtained. Small amounts of alkylbenzene can remain present after the reaction but dialkylated benzene usually does not occur unless the process conditions are altered to favor the monoalkylation reaction. Only negligible amounts of olefin usually remain present at the completion of the reaction when the yield of trialkylated benzene is above 90-95%. The process provides a method of generating benzene trialkylates with no requirement of a complicated separation procedure to isolate the trialkylates from dialkylates, monoalkylates, and other side reaction end products.

The borontrifluoride carboxylic acid complex can be recovered and reused. In order to recycle the catalyst it should be kept free from moisture. This can more readily be accomplished by equipping the reactor with a condensor and drying tube or similar equivalent apparatus. If the catalyst is kept substantially free of moisture contamination usually no further purification process is required before reuse. Reuse of the catalyst is not advisable if water is present because of the formation of borontrifluoride water complexes. These complexes do not catalyze the alkylation reaction and their presence reduces the effectiveness of the catalyst solution.

The reaction can be implemented as a batch or continuous process. In a batch process the olefin and alkylbenzene are charged to a reaction zone maintained at the appropriate temperature and the catalyst, after preparation in a separate reaction zone, is added to effect the reaction. In a continuous process the olefin and alkylbenzene could be charged to one end of a reaction zone, the catalyst introduced after preparation in a separate zone, and after reaction, product and catalyst withdrawn from the other end of the zone, the liquid catalyst being continuously recycled back to the initial end of the reaction zone. Periodic replacement of the catalyst from the catalyst preparation zone would assure its optimal efficiency. The alkylation could be conducted as a vapor phase reaction when high molecular weight polymers of olefins are not used.

EXAMPLE 1

One mole each of toluene and of dodecene-1 was added with vigorous stirring to a two liter glass reactor, equipped with a reflux condenser and drying tube, containing one-half mole of 1:2 mole ratio borontrifluoride formic acid complex. The temperature of the reaction was maintained at 25°-35° C. Stirring of the reaction mixture was continued for twenty-four hours after cooling to room temperature. After phase separation on standing, the catalyst layer was siphoned off and the alkylate layer was purified by washing with water and drying over anhydrous sodium sulfate. Distillation under vacuum gave no olefin recovery but residual toluene was collected. The residue of the distillation was identified by ultraviolet and infrared spectroscopy as 2,4-dodecyl 1-methyl benzene. A total of 200 grams of product was recovered equivalent to a 93% yield. Physical properties of the product are listed in Table A.

This example illustrates the dialkylation of toluene with substantially no intra or inter molecular rearrangement of alkyl groups.

Table A

| Viscosity | |
|---|---|
| SSU at 99° C. | 35 |
| SSU at 38° C. | 62 |
| SSU at −18° C. | 1036 |
| SSU at −34° C. | 4974 |
| Pour Point | −56.7° C. still pouring |
| Gravity, API | 32.6° |
| Flash | 173.9° C. |
| Total Acid Number | 1.8 mg KOH/g |
| Total Base Number | Neutral |

EXAMPLE 2

Two moles of toluene and 2 moles of $C_{11}$–$C_{14}$ α-olefins were added with vigorous stirring of a two liter glass reactor equipped as in Example 1 containing one mole of 1:2 borontrifluoride formic acid complex. The temperature of the reaction was maintained at 30° C. to 55° C. After standing overnight the catalyst layer was withdrawn. Two moles of $C_{11}$–$C_{14}$ α-olefins and one mole of 1:2 borontrifluoride formic acid complex were added to the alkylate layer. The temperature of the reaction was maintained at 45° C. to 55° C. Stirring of the reaction mixture was continued for 72 hours. Separation and purification of product were as in Example 1. Product recovered was equivalent to an 86% yield of dialkylated toluene. Physical properties of the product are listed in Table B with those of a typical commercial synthetic oil. This example illustrates production of a synthetic lubricant with properties comparable to those currently available.

Table B

| | Dialkylated Toluene | Commercial Synthetic Oil |
|---|---|---|
| Viscosity | | |
| SSU at 99° C. | 44.6 | 45.7 |

Table B-continued

| | Dialkylated Toluene | Commercial Synthetic Oil |
|---|---|---|
| SSU at 38° C. | 147 | 151 |
| CST at −40° C. | 11246 | 8500 |
| Viscosity Index | 130 | 144 |
| Pour Point, maximum | −51.1° C. | −53.9° C. |
| Flash, minimum | 223.9° C. | 229.4° C. |

I claim:

1. Process of dialkylating alkylbenzene which comprises contacting olefin and alkylbenzene at a temperature of 10° C. to 90° C. in the presence of a borontrifluoride carboxylic acid complex.

2. The process of claim 1 wherein the molar ratio of borontrifluoride:carboxylic acid varies from about 1:1 to 1:3 in the complex.

3. The process of claim 1 wherein the acid component of the borontrifluoride carboxylic acid complex is an aliphatic carboxylic acid containing one to eight carbon atoms.

4. The process of claim 1 wherein formic acid comprises the acid component of the borontrifluoride carboxylic acid complex.

5. The process of claim 1 wherein the olefin is an α-olefin of $C_8$ to $C_{40}$.

6. The process of claim 1 wherein the alkylbenzene has a straight chained substituent.

7. The process of claim 1 wherein the amount of olefin reactant is equal to or exceeds the amount of alkylbenzene reactant.

8. The process of claim 1 wherein the dialkylation reaction is maintained at a temperature of 10° C. to 80° C.

9. The process of claim 1 wherein an excess of $C_{12}$–$C_{20}$ α-olefin is contacted with monoalkylbenzene at a temperature of 10° C. to 80° C. at atmospheric pressure with continued stirring for a minimum of about 24 hours after the reaction mixture cools to room temperature.

10. The process of claim 9 wherein dodecene-1 comprises the olefin and toluene comprises the alkylbenzene.

* * * * *